US012577340B2

(12) United States Patent
Stippschild-Boxler et al.

(10) Patent No.: US 12,577,340 B2
(45) Date of Patent: Mar. 17, 2026

(54) STORAGE STABLE TWO-COMPONENT DUAL CURE DENTAL COMPOSITION

(71) Applicant: Solventum Intellectual Properties Company, Maplewood, MN (US)

(72) Inventors: Andrea Stippschild-Boxler, Landsberg (DE); Christoph H. Thalacker, Weilheim (DE); Bernd Anich, Andechs (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 944 days.

(21) Appl. No.: 17/292,817

(22) PCT Filed: Nov. 12, 2019

(86) PCT No.: PCT/IB2019/059717
§ 371 (c)(1),
(2) Date: May 11, 2021

(87) PCT Pub. No.: WO2020/100041
PCT Pub. Date: May 22, 2020

(65) Prior Publication Data

US 2021/0395419 A1 Dec. 23, 2021

(30) Foreign Application Priority Data

Nov. 14, 2018 (EP) .................................... 18206112

(51) Int. Cl.

| | |
|---|---|
| ***C08F 222/10*** | (2006.01) |
| ***A61C 5/62*** | (2017.01) |
| ***A61K 6/62*** | (2020.01) |
| ***A61K 6/71*** | (2020.01) |
| ***A61K 6/831*** | (2020.01) |
| ***A61K 6/84*** | (2020.01) |
| ***C08F 4/10*** | (2006.01) |
| ***C08F 4/34*** | (2006.01) |

(52) U.S. Cl.
CPC .......... *C08F 222/1065* (2020.02); *A61C 5/62* (2017.02); *A61K 6/62* (2020.01); *A61K 6/71* (2020.01); *A61K 6/831* (2020.01); *A61K 6/84* (2020.01); *C08F 4/10* (2013.01); *C08F 4/34* (2013.01); *C08F 222/102* (2020.02)

(58) Field of Classification Search
None
See application file for complete search history.

(56) References Cited

U.S. PATENT DOCUMENTS

| | | | |
|---|---|---|---|
| 3,729,313 | A | 4/1973 | Smith |
| 3,741,769 | A | 6/1973 | Smith |
| 3,808,006 | A | 4/1974 | Smith |
| 4,250,053 | A | 2/1981 | Smith |
| 4,259,075 | A | 3/1981 | Yamauchi |
| 4,394,403 | A | 7/1983 | Smith |
| 4,499,251 | A | 2/1985 | Omura |
| 4,537,940 | A | 8/1985 | Omura |
| 4,539,382 | A | 9/1985 | Omura |
| 4,642,126 | A | 2/1987 | Zador |
| 4,652,274 | A | 3/1987 | Boettcher |
| 4,695,251 | A | 9/1987 | Randklev |
| 4,737,593 | A | 4/1988 | Ellrich |
| 4,795,823 | A | 1/1989 | Schmitt |
| 4,872,936 | A | 10/1989 | Engelbrecht |
| 5,130,347 | A | 7/1992 | Mitra |
| 5,501,727 | A | 3/1996 | Wang |
| 5,530,038 | A | 6/1996 | Yamamoto |
| 5,545,676 | A | 8/1996 | Palazzotto |
| 5,688,883 | A | 11/1997 | Klee |
| 5,847,025 | A | 12/1998 | Moszner |
| 5,918,772 | A | 7/1999 | Keller |
| 5,944,419 | A | 8/1999 | Streiff |

(Continued)

FOREIGN PATENT DOCUMENTS

| | | |
|---|---|---|
| DE | 102010003883 | 10/2011 |
| EP | 0712622 | 5/1996 |

(Continued)

OTHER PUBLICATIONS

Antonucci, "New initiator systems for dental resins based on ascorbic acid", Journal of Dental Research, Sep. 1979, vol. 58, No. 9, pp. 1887-1899.

(Continued)

*Primary Examiner* — Robert T Butcher

(57) ABSTRACT

The invention relates to a two-part dual cure dental composition with improved stability toward discoloration and premature polymerization. The dental composition comprises a Base Part and a Catalyst Part, the Base Part comprising polymerizable component(s) without an acidic moiety, optionally polymerizable component(s) with an acidic moiety, filler(s), transition metal component(s), peroxide component(s), stabilizer component(s) comprising a free-radical moiety, the Catalyst Part comprising polymerizable component(s) without an acidic moiety, filler(s), ascorbic acid component, photo-initiator system, stabilizer component(s) comprising a phosphite or sulfite moiety. The dental composition is in particular useful as bulk fill dental composite, dental resin cement, core build-up dental material or self- and dual cure dental adhesive. The invention further relates to an initiator system and the use of a stabilizer comprising a free-radical moiety.

20 Claims, No Drawings

(56) References Cited

U.S. PATENT DOCUMENTS

| | | | |
|---|---|---|---|
| 5,998,495 | A | 12/1999 | Oxman |
| 6,025,406 | A | 2/2000 | Oxman |
| 6,043,295 | A | 3/2000 | Oxman |
| 6,084,004 | A | 7/2000 | Weinmann |
| 6,187,833 | B1 | 2/2001 | Oxman |
| 6,387,981 | B1 | 5/2002 | Zhang |
| 6,444,725 | B1 | 9/2002 | Trom |
| 6,458,868 | B1 | 10/2002 | Okada |
| 6,572,693 | B1 | 6/2003 | Wu |
| 6,730,156 | B1 | 5/2004 | Windisch |
| 6,765,036 | B2 | 7/2004 | Dede |
| 6,899,948 | B2 | 5/2005 | Zhang |
| 6,998,111 | B2 | 2/2006 | Klee |
| 8,501,834 | B2 | 8/2013 | Maletz |
| 2004/0206932 | A1 | 10/2004 | Abuelyaman |
| 2005/0203199 | A1* | 9/2005 | Moszner .................. C08F 2/50 522/6 |
| 2005/0252413 | A1 | 11/2005 | Kangas |
| 2005/0252414 | A1 | 11/2005 | Craig |
| 2005/0256223 | A1 | 11/2005 | Kolb |
| 2006/0187752 | A1 | 8/2006 | Keller |
| 2007/0090079 | A1 | 4/2007 | Keller |
| 2012/0010357 | A1* | 1/2012 | Bruchmann ......... C08G 83/005 528/73 |
| 2016/0355664 | A1 | 12/2016 | Zuijderduin |
| 2018/0221249 | A1 | 8/2018 | Fik |

FOREIGN PATENT DOCUMENTS

| | | |
|---|---|---|
| EP | 1051961 | 11/2000 |
| WO | WO 2003-063804 | 8/2003 |
| WO | WO 2005-016783 | 2/2005 |
| WO | WO 2007-104037 | 9/2007 |
| WO | WO 2009-061884 | 5/2009 |
| WO | WO 2009-151957 | 12/2009 |
| WO | WO 2010-123800 | 10/2010 |
| WO | WO 2015-073246 | 5/2015 |
| WO | WO 2016-007453 | 1/2016 |
| WO | 2017100231 A1 | 6/2017 |
| WO | WO 2017-100231 | 6/2017 |
| WO | WO 2019-092580 | 6/2019 |
| WO | WO 2019-211724 | 11/2019 |

OTHER PUBLICATIONS

International Search Report for PCT International Application No. PCT/IB2019/059717, mailed on Feb. 26, 2020, 4 pages.

* cited by examiner

STORAGE STABLE TWO-COMPONENT DUAL CURE DENTAL COMPOSITION

CROSS REFERENCE TO RELATED APPLICATIONS

This application is a national stage filing under 35 U.S.C. 371 of PCT/IB2019/059717, filed 12 Nov. 2019, which claims the benefit of European Patent Application No. 18206112.7, filed 14 Nov. 2018, the disclosures of which are incorporated by reference herein in their entireties.

FIELD OF THE INVENTION

The invention relates to a two-part dual cure dental composition with improved stability toward discoloration and premature polymerization.

The dental composition is in particular useful as bulk fill dental composite, dental resin cement, core build-up dental material or self- and dual cure dental adhesive.

BACKGROUND

Generally, one-part and two-part curable dental compositions are known.

For curing the one-part or two-part dental compositions, different kinds of initiator systems are suggested.

For preventing premature polymerization of the curable components, some of these compositions contain stabilizing agents or other means for improving the storage stability.

J. M. Antonucci et al. describe the use of an initiator system involving a peroxide, an ascorbic acid derivative, and a copper salt in J. M. Antonucci, C. L. Grams, D. J. Termini: "New initiator systems for dental resins based on ascorbic acid", J. Dent. Res. 1979, 58, 1887-1899.

U.S. Pat. No. 5,501,727 (3M) relates to a curable dental composition comprising an ethylenically unsaturated moiety, an oxidizing agent and metal complexed ascorbic acid.

U.S. Pat. No. 5,688,883 (Dentsply) refers to a polymerizable composition formed by mixing a liquid and a powder composition, where the liquid includes a peroxide, and the powder comprises a proton donor (e.g. an ascorbic acid derivative) and a metal containing compound.

U.S. Pat. No. 6,998,111 (Dentsply) describes storage stable polymerizable compositions including a peroxide, a metal containing material, and a protected reducing agent (e.g. ascorbic acid bearing protecting groups).

U.S. Pat. No. 5,847,025 (Ivoclar) describes a light-curing composite material which is characterized by a content of anaerobic stabilizer and/or stable organic radicals and which has a reduced light sensitivity and an improved vacuum stability.

EP 2 374 445 A2 (Voco) describes a dual-cure, multicomponent dental composition.

WO 2016/007453 A1 (3M) describes a two-component self-adhesive dental composition, process of production and use thereof.

WO 2017/100231 A1 (3M) describes a two-component self-adhesive dental composition, storage stable initiator system, and use thereof.

DE 10 2010 003 883 A1 (Voco) describes a photopolymerizable dental composition comprising: (a) a photopolymerizable monomer comprising acrylate and methacrylate, (b) a photo initiator, (c) a molecular weight regulator comprising a compound, which is reacted with a radical of a monomer of the component (a), where the reaction is carried out by abstracting a hydrogen-radical from the molecular weight regulator in allylic position; and (e) at least one inorganic filler.

US 2005/203199 A1 (Moszner et al.) refers to dental materials which contain radically polymerizable organic binder, a polymerization initiator, and an accelerator. In addition, the materials may include a polymerizable UV absorber and a polymerizable inhibitor to prevent premature spontaneous polymerization.

US 2018/0221249 A1 (Fik et al.) describes aqueous dental adhesive compositions comprising polymerizable compounds with a polymerizable double bond, an initiator system, a solvent mixture and a certain hydroquinone stabilizer. It is described that the use of other stabilizers may impart the stability of dental compositions but give rise to discoloration problems.

SUMMARY OF INVENTION

There is generally a need for a curable dental composition with appropriate curing kinetics, particularly a curable dental composition which can be cured sufficiently fast to obtain a product having appropriated physical properties like flexural strength and E-modulus.

Further, the curable dental composition should be sufficiently storage stable.

A sufficient storage stability is typically achieved by adding an appropriate amount of a suitable stabilizer.

For stabilizing curable compositions containing a highly reactive initiator system, typically a high amount of stabilizer is needed.

However, using high amounts of stabilizers might help to stabilize the composition from a rheological point of view, but may cause other problems, like discoloration over time.

Thus, particularly there is a need for a dental composition with appropriate curing properties, which is sufficiently storage stable and which does not show an unacceptable discoloration during storage.

One or more of the above objects are addressed by the invention described in the present text.

In one embodiment the invention features a dental composition comprising a Base Part and a Catalyst Part to be mixed before use, the Base Part comprising
- polymerizable component(s) without an acidic moiety,
- optionally polymerizable component(s) with an acidic moiety,
- filler(s),
- transition metal component(s),
- peroxide component(s),
- stabilizer component(s) comprising a free-radical moiety, the Catalyst Part comprising
- polymerizable component(s) without an acidic moiety,
- filler(s),
- ascorbic acid component,
- photo-initiator system,
- stabilizer component(s) comprising a phosphite or sulfite moiety as described in the present text and claims.

In another embodiment, the invention relates to a dental composition for use in a process comprising the steps of mixing the Base Part and the Catalyst Part to obtain a Mixed Part, applying at least a portion of the Mixed Part to the surface of hard dental tissue, optionally applying radiation to the portion of the Mixed Part as described in the present text and claims.

A further embodiment of the invention is directed to a kit of parts comprising the dental composition and at least one of the following items: dental filling composite; dental sealant; dental cement; dental mill blank; dental etchant; dental adhesive; dental try-in paste; dental fibre post as described in the present text and claims.

The invention is also related to the use of a stabilizer comprising a free-radical moiety for stabilizing an initiator system comprising peroxide component in combination with a transition metal ion component.

A further embodiment relates to an initiator system comprising transition metal component(s), peroxide component(s), stabilizer component(s) comprising a free-radical moiety, ascorbic acid component(s), a photo-initiator system, and stabilizer component(s) comprising a phosphite or sulfite moiety, wherein the components are as described in the present text.

Unless defined differently, for this description the following terms shall have the given meaning:

A "dental composition" or a "composition for dental use" or a "composition to be used in the dental field" is a composition which can and is to be used in the dental field. In this respect, the composition should be not detrimental to the patients' health and thus free of hazardous and toxic components being able to migrate out of the composition.

Dental compositions are typically curable compositions, which can be hardened at ambient conditions, including a temperature range of 15 to 50° C. or 20 to 40° C. within a time frame of 30 min or 20 min or 10 min. Higher temperatures are not recommended as they might cause pain to the patient and may be detrimental to the patient's health.

Dental compositions are typically provided to the practitioner in rather small volumes, that is volumes in the range of 0.1 to 100 ml or 0.5 to 50 ml or 1 to 30 ml. Thus, the storage volume of useful packaging devices is within these ranges.

"One-part composition" means that all components of the composition are present in the composition during storage and use. That is, the composition to be applied or used is not prepared by mixing different parts of the composition before use. In contrast to one-part compositions, two-part or multi-part compositions are typically formulated as powder/liquid, liquid/liquid or paste/paste compositions and are provided to the practitioner in the form of a kit of parts.

The term "compound" is a chemical substance which has a particular molecular identity or is made of a mixture of such substances, including polymeric substances.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

A "polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (meth)acrylate group.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

"Polymer" or "polymeric material" are used interchangeably to refer to a homopolymer, copolymer, terpolymer etc.

As used herein, "(meth)acryl" is a shorthand term referring to "acryl" and/or "methacryl". For example, a "(meth) acryloxy" group is a shorthand term referring to either an acryloxy group (i.e., $CH_2$═CH—C(O)—O—) and/or a methacryloxy group (i. e., $CH_2$═$C(CH_3)$—C(O)—O—).

An "polymerizable component with an acidic moiety" is meant to include monomers, oligomers, and polymers having ethylenic unsaturation and acid and/or acid-precursor functionality.

Acidic-precursor functionalities include, e.g. anhydrides, acid halides and pyrophosphates.

The acidic group preferably comprises one or more carboxylic acid residues, such as —COOH or —CO—O—CO—, phosphoric acid residues, such as —O—P(O)(OH)OH, phosphonic acid residues or sulfonic acid residues, such as —$SO_3H$, or sulfinic acid residues such as —$SO_2H$.

A component comprising an "ascorbic acid moiety" is a component comprising the following structural element:

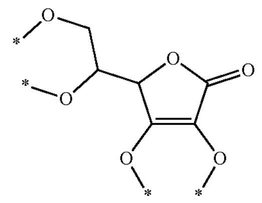 [SMILES: *OCC(O*)C1OC(=O)C(O*)=C1O*]

wherein the symbol "*" indicates a connection to another chemical moiety or atom.

A "solvent" means a liquid which is able to at least partially disperse or dissolve a component at ambient conditions (e.g. 23° C.). A solvent typically has a viscosity below about 5 or below about 1 or below about 0.1 Pa*s.

As used herein, "hardening" or "curing" a composition are used interchangeably and refer to polymerization and/or crosslinking reactions including, for example, photopolymerization reactions and chemical polymerization techniques (e. g., ionic reactions or chemical reactions forming radicals effective to polymerize ethylenically unsaturated compounds) involving one or more materials included in the composition.

A "self-cure dental composite material" means a material which can harden without applying radiation. Such a material typically contains a redox-initiator system comprising an oxidizing component (such as a peroxide) and a reducing component (such as an amine). During storage a self-cure dental composite material is typically provided as a kit of parts where the components of the redox-initiator system are separated from each other.

A "dual-cure dental composite material" means a self-cure dental composite material which contains in addition a photo-initiator system.

By "paste" is meant a soft, viscous mass of solids (i.e. particles) dispersed in a liquid.

As used herein, a "dental surface" or "dental hard tissue" refers to tooth structures (e. g., enamel, dentin, and cementum) and bone.

A "dental restoration" refers to a material for restoring the function of missing tooth structure. Examples of dental restorations include dental filling materials, provisional crown and bridge materials, dental crowns and bridges, inlays, onlays, veneers, root canal fillers and dental posts.

A "self-etching composition" refers to a composition which bonds to a dental surface without pre-treating the dental surface with an etchant. Preferably, a self-etching composition can also function as a self-adhesive primer wherein no separate etchant or primer is used or be a self-adhesive composition.

A "self-adhesive composition" refers to a composition that is capable of bonding to a dental surface without pre-treating the dental surface with a primer or bonding agent. Preferably, a self-adhesive composition is also a self-etching composition wherein no separate etchant is used.

An "untreated dental surface" refers to a tooth or bone surface that has not been treated with an etchant, primer, or bonding agent prior to application of a self-etching adhesive or a self-adhesive composition.

However, it may have been treated mechanically with a dental bur, grinding or polishing media, pumice etc.

An "unetched" dental surface refers to a tooth or bone surface that has not been treated with an etchant prior to application of a self-etching adhesive or a self-adhesive composition.

A "functionalised silane compound" is a silane compound bearing one or more moieties, which is able to undergo chemical reactions beyond condensation with OH-moieties of other silanes or on the surface of a filler. Examples of functionalised silane compounds include amino or (meth) acrylate functionalised silanes, like 3-aminopropyl trimethoxysilane or 3-(meth)acryloxypropyl trimethoxysilane.

A composition is characterized as "dual-curing", if it contains one or more initiator systems allowing the composition to be cured either by radiation or without radiation by a redox reaction, i.e. by a self-cure mechanism.

"Radiation curable" shall mean that the component (or composition, as the case may be) can be cured by applying radiation, preferably electromagnetic radiation with a wavelength in the visible light spectrum under ambient conditions and within a reasonable time frame (e.g. within about 60, 30 or 10 seconds).

"Ambient conditions" mean the conditions which the composition described in the present text is usually subjected to during storage and handling. Ambient conditions may, for example, be a pressure of 900 to 1,100 mbar, a temperature of 10 to 40° C. and a relative humidity of 10 to 100%. In the laboratory, ambient conditions are typically adjusted to 20 to 25° C. and about 50% relative humidity.

A material or composition is "essentially or substantially free of" a certain component within the meaning of the invention, if the material or composition does not contain said component as an essential feature. Thus, said component is not willfully added to the composition or material either as such or in combination with other components or ingredient of other components. A composition or material being essentially free of a certain component usually contains the component in an amount of less than 1 wt. % or less than 0.1 wt. % or less than 0.01 wt. % with respect to the whole composition or material. Ideally the composition or material does not contain the said component at all. However, sometimes the presence of a small amount of the said component is not avoidable e.g. due to impurities.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and used in the specification and claims are to be understood as number as such and also as being modified by the term "about."

The term "about" can allow for a degree of variability in a value or range, e.g. within 10% or within 5% or within 1% of a given value or a given limit of a range.

The terms "comprise" or "contain" and variations thereof do not have a limiting meaning where these terms appear in the description and claims. The term "comprise" shall include also the terms "consist essentially of" and "consists of". "Consisting essentially of" means that specific further components can be present, which do not materially affect the essential characteristics of the article, composition or method. "Consisting of" means that no further components are present.

"And/or" means one or both. E.g., the expression component A and/or component B refers to a component A alone, component B alone, or to both component A and component B.

DETAILED DESCRIPTION

It has been found that the dental composition described in the present text has a couple of advantageous properties.

The dental composition comprises an initiator system with high reactivity and fast curing kinetics, which makes it suitable in the dental filed, in particular for dental compositions where a fast and secure curing is desired.

In this respect, the initiator system comprises two parts, a photo-initiator system and a redox-initiator system.

The redox-initiator system becomes active upon mixing the Base Part and the Catalyst Part.

The photo-initiator system becomes active upon exposure of the composition to radiation.

The combination of both systems enables a fast and secure curing of the dental composition, even under difficult conditions.

However, using such a highly reactive initiator system may have a negative impact on the storage stability of the composition or respective parts thereof.

This topic is typically addressed by adding a stabilizer component.

However, if well-known stabilizing components, such as phenolic stabilizers (e.g. butylated hydroxytoluene; BHT) or hydroquinone stabilizers (e.g. hydroquinone monomethyl ether; MEHQ) were used at usual concentrations of up to several hundred ppm, the dental composition or respective parts thereof showed an undesired premature polymerization.

If the concentration of these well-known stabilizing components was increased, an undesired discoloration of the dental composition or respective parts thereof was observed.

These issues can be addressed by using stabilizing component(s) comprising a free-radical moiety.

It was found that these stabilizing components are particularly useful for stabilizing curable compositions containing peroxide components, even in the presence of transition metal components.

It was also found that for achieving a long-term stability of the composition and respective parts thereof, only a small amount of these stabilizing components is needed.

Thus, the dental composition and the respective parts thereof described in the present text are sufficiently storage stable and do not show discoloration, even after a long storage time.

In addition to the stabilizing components comprising a free radical moiety, the dental composition comprises further stabilizing components. These further stabilizing components comprise sulfite or phosphite moieties.

It was found that these stabilizing components are particularly useful for stabilizing an initiator system comprising an ascorbic acid component in combination with a photo-initiator system.

Further, the dental composition obtained after curing shows appropriate physical properties, such as flexural strength and E-modulus.

Thus, the dental composition described in the present text comprises curable components, fillers, a highly reactive initiator system comprising photo-initiator components and redox-initiator components and two kinds of stabilizer components.

The invention described in the present text comprises a Base Part and a Catalyst Part and can such be regarded as a two-part dental composition.

The compositions contained in the Base Part and the Catalyst Part are intended to be mixed before use to obtain a curable dental composition.

The Base Part and the Catalyst Part are typically provided in mixing ratio of 10:1 to 1:1 or 5:1 to 1:1 or 2:1 to 1:1 with respect to volume.

A mixing ratio of 1:1 with respect to volume is sometimes preferred as it allows a more homogeneous mixing of the respective parts.

The dental composition obtained after mixing the Base Part and the Catalyst Part typically has a viscosity in the range of 10 to 70 Pa*s at 28° C.

A dental composition having a viscosity in such a range can be easily expensed from a static mixing cannula and applied to the surface of a tooth structure.

Further, a dental composition having a viscosity in such a range can be used as a flowable bulk fill dental composite material, a dental resin cement or a self- and dual cure dental adhesive material.

The composition contained in the Base Part typically has a viscosity in the range of 5 to 60 Pa*s at 23° C.

A Base Part having a viscosity in such a range can easily be mixed by using a static mixing cannula.

The composition contained in the Base Part typically has a pH-value in the range of 2 to 5, if brought in contact with water (e.g. a wet pH-sensitive paper). Thus, the composition contained in the Base Part is typically acidic.

The Base Part is typically provided as a paste.

The Base Part comprises polymerizable component(s) without an acidic moiety.

Suitable polymerizable component(s) without acidic moiety(s) can be characterized by the following formula:

$$A_nBA_m$$

with A being an ethylenically unsaturated group attached to backbone B, such as a (meth)acryloyl moiety, B being selected from (i) linear or branched $C_1$ to $C_{12}$ alkyl, (ii) $C_6$ to $C_{12}$ aryl, optionally substituted with other functional groups (e.g. OH), or (iii) organic group having 4 to 20 carbon atoms bonded to one another by one or more ether, ester, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or poly-acrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, diurethane dimethacrylate, sometimes referred to as UDMA (mixture of isomers, e.g. Rohm Plex™ 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetra-methacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-methacryloxy) ]-p-propoxyphenyldimethylmethane, dimethacrylates of ethoxylated bisphenol A with 2-10 ethoxy units (e.g. BisEMA-6) and trishydroxyethyl-isocyanurate trimethacrylate; bis-acrylates and bis-methacrylates of polyethylene glycols of molecular weight 200-500, copolymerizable mixtures of acrylated monomers (see e.g. U.S. Pat. No. 4,652,274 (Boettcher et al.)), and acrylated oligomers (see e.g. U.S. Pat. No. 4,642,126 (Zador et al.)); and vinyl compounds such as styrene, diallyl phthalate, divinyl succinate, divinyl adipate and divinylphthalate; polyfunctional (meth)acrylates comprising urethane, urea or amide groups.

Examples of polyether (meth)acrylates include dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono(meth)acrylate, and the like.

The molecular weight of these compounds is typically less than 20,000 g/mol, particularly less than 15,000 g/mol, and in particular less than 10,000 g/mol.

Further examples for polymerizable component(s) are the di(meth)acrylate derived from tricyclodecane-dimethanol (which is typically a mixture of isomers), reaction products of tricyclodecane-dimethanol with isocyanatoethyl (meth)acrylate, reaction products of tricyclodecane-diisocyanate with hydroxyethyl (meth)acrylate or hydroxypropyl (meth)acrylate, such as bis[3[4]-methacryl-oxymethyl-8(9)-tricyclo[5.2.1.$0^{2,6}$]decylmethyl triglycolate and urethane (meth)acrylates and di(meth)acrylates of bishydroxymethyltricyclo-(5.2.1.$0^{2,6}$)decane. These kind of methacrylic esters are described in U.S. Pat. No. 4,795,823 (Schmitt et al.).

Polymerizable monomers comprising a hydroxyl moiety can also be added.

Suitable compounds include 2-hydroxyethyl methacrylate (HEMA), 2- or 3-hydroxypropyl (meth)-acrylate, 4-hydroxybutyl (meth)acrylate, 5-hydroxypentyl (meth)acrylate, 6-hydroxyhexyl (meth)acrylate, 10-hydroxydecyl (meth) acrylate, 1,2- or 1,3- and 2,3-dihydroxypropyl (meth)acrylate, 2-hydroxypropyl-1,3-di(meth)acrylate, 3-hydroxypropyl-1,2-di(meth)acrylate, N-(meth)acryloyl-1,2-dihydroxypropylamine, N-(meth)acryloyl-1,3-dihydroxypropylamine, 1-phenoxy-2-hydroxypropyl (meth) acrylate, 1-naphthoxy-2-hydroxypropyl (meth)acrylate.

2-Hydroxyethyl (meth)acrylate, 2-hydroxypropyl (meth) acrylate and 2,3-dihydroxypropyl (meth)acrylate are sometimes preferred.

If desired, it is also possible to use brominated components, like those which are described in EP patent application 17200519.1. The content of this reference is herewith incorporated by reference.

If brominated components are desired, in particular those components were found to be useful, which comprise an aromatic moiety selected from brominated resorcinol, catechol, tyrosol, benzoic acid, or phenol moieties.

Mixtures of two or more of these free radically polymerizable materials can be used, if desired.

The polymerizable component without an acidic moiety contained in the Base Part is typically present in the following amount(s):

Lower limit: at least 5 or at least 10 or at least 20 wt. %;

Upper limit: utmost 70 or utmost 60 or utmost 50 wt. %;

Range: 5 to 70 or 10 to 60 or 20 to 50 wt. %;

wt. % with respect to the amount of the Base Part.

The Base Part may also comprise polymerizable component(s) with an acidic moiety.

The polymerizable component having an acidic moiety can be represented by the following formula $A_nBC_m$ B being a backbone group, such as (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, A being an ethylenically unsaturated group attached to the backbone group, such as a (meth)acryloyl moiety, C being an acidic group attached to the backbone group, with m, n=1, 2, 3, 4, 5 or 6, wherein the acidic group comprises one or more carboxylic acid or anhydride residues, such as —COOH or —CO—O—CO—, phosphoric acid residues, such as O—P(O)(OH)OH, phosphonic acid residues or sulfonic acid residues, such as $SO_3H$ or sulfinic acid residues, such as $SO_2H$.

Specific examples of ethylenically unsaturated acidic compounds include, but are not limited to glycerol phosphate mono(meth)acrylates, glycerol phosphate di(meth) acrylates, hydroxyethyl (meth)acrylate phosphates, bis glycerol phosphate di(meth)acrylates, bis((meth)acryloxyethyl) phosphate, ((meth)acryloxypropyl) phosphate, bis((meth) acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, di or tri(meth)acrylated citric acid, poly(meth)acrylated oligomaleic acid, poly(meth)acrylated polymaleic acid, poly(meth)acrylated poly(meth) acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like.

The reaction products of (meth)acrylic acid with alkane diols (e.g. $C_2$ to $C_{20}$ or $C_2$ to $C_{12}$ or $C_6$ to $C_{10}$) and phosphorous oxide were found to be suitable as well.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example in US 2004/0206932 A1 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Fuchigami et al.) and EP 1 051 961 A1 (Hino et al.).

Typical compositions also include an ethylenically unsaturated acidic compound with at least one phosphoric acid group (e.g. P—OH moiety).

Examples of preferred phosphoric acid group-containing polymerizable monomer include 6-(meth)acryloxyhexyl dihydrogenphosphate, 7-(meth)acryloxyheptyl dihydrogenphosphate, 8-(meth)acryloxyoctyl dihydrogenphosphate, 9-(meth)acryloxynonyl dihydrogenphosphate, 10-(meth) acryloxydecyl dihydrogenphosphate, 11-(meth)acryloxyundecyl dihydrogenphosphate, 12-(meth)acryloxydodecyl dihydrogenphosphate, 16-(meth)acryloxyhexadecyl dihydrogenphosphate, 20-(meth)acryloxyeicosyl dihydrogenphosphate, bis[6-(meth)acryloxyhexyl] hydrogenphosphate, bis[8-(meth)acryloxyoctyl] hydrogenphosphate, bis[9-(meth)acryloxynonyl] hydrogenphosphate, bis[10-(meth) acryloxydecyl] hydrogenphosphate, 1,3-di(meth)acryloxypropyl dihydrogenphosphate, 2-(meth)acryloxyethylphenyl hydrogenphosphate, 2-(meth)acryloxyethyl-2-bromoethyl hydrogenphosphate, (5-methacryloxy)pentyl-3-phosphonopropionate, (6-methacryloxy)hexyl-3-phosphonopropionate, (10-methacryloxy)decyl-3-phosphonopropionate, (6-methacryloxy)hexyl-3-phosphonoacetate, (10-methacryloxy)decyl-3-phosphonoacetate, 2-methacryloxyethyl (4-methoxyphenyl) hydrogenphosphate and 2-methacryloxypropyl (4-methoxyphenyl) hydrogenphosphate and mixtures thereof.

Mixtures of different components comprising an acidic moiety can be used, if desired.

The presence of polymerizable component(s) with an acidic moiety helps to increase the etching properties of the composition.

If present, the polymerizable component with an acidic moiety contained in the Base Part is typically present in the following amount:

Lower limit: at least 0.5 or at least 1 or at least 2 wt. %;
Upper limit: utmost 20 or utmost 15 or utmost 10 wt. %;
Range: 0.5 to 20 or 1 to 15 or 2 to 10 wt. %;
wt. % with respect to the amount of the Base Part.

The Base Part further comprises filler(s).

Fillers may be selected from one or more of a wide variety of materials suitable for incorporation in compositions used for dental applications.

The filler(s) which may be used in the compositions of the present text is preferably finely divided. The filler(s) can have a unimodal or polymodal (e.g., bimodal) particle size distribution. Typically, the maximum particle size (the largest dimension of a particle, generally, the diameter) of the filler(s) is less than 20 μm, more typically less than 10 μm, and most preferably less than 5 μm. Typically, the average primary particle size of the filler(s) is less than 0.1 μm, and more typically less than 0.075 μm.

The filler(s) should be nontoxic and suitable for use in the mouth or a patient. The filler(s) can be radiopaque or radiolucent. The filler typically is substantially insoluble in water.

The compositions may include filler(s) comprising or consisting essentially of or consisting of an inorganic material.

Examples of suitable inorganic fillers are naturally occurring or synthetic materials including, but not limited to: quartz; glasses derived from, e.g., Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas).

Pyrogenic or precipitated silica has been found to be particularly useful.

Suitable pyrogenic silica fillers typically have a specific surface area (BET) of 100 to 400 $m^2/g$.

Examples of non-surface treated fillers which can be used include AEROSIL™, including "OX 50," "90", "130", "150", "200", "300", and "380" silicas (Evonik Industries AG, Essen, Germany), and Cab-O-Sil, including "LM-150", "M-5", "H-5", "EH-5" silicas (Cabot Corp., Tuscola, Ill.), and HDK™, including "S13", "V15", "N20", "T30", "T40" silicas (Wacker-Chemie AG, Munich, Germany), and Orisil™, including "200", "300", "380" silicas (Orisil, Lviv, Ukraine).

Suitable filler(s) also include nano-sized silica particles, nano-sized metal oxide particles, and combinations thereof. Nanofillers are described e.g. in US 2005/0252413 (Kangas et al.); 2005/0252414 (Craig et al.); and 2005/0256223 (Kolb et al.).

Other suitable fillers are disclosed in U.S. Pat. No. 6,387,981 (Zhang et al.), U.S. Pat. No. 6,572,693 (Wu et al.) U.S. Pat. No. 6,730,156 (Windisch), U.S. Pat. No. 6,899,948 (Zhang) as well as WO 03/063804 (Wu et al.).

Filler(s) which can also be used and which provide radiopacity to the materials described in the present text include heavy metal oxide(s) and fluoride(s). As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colours to the neutral tooth colour of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. yttrium trifluoride and ytterbium trifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than 200 nm, and more preferably are less than 90 nm in average diameter.

Other suitable fillers to increase radiopacity are salts of barium and strontium especially strontium sulphate and barium sulphate.

The surface of the filler particles can be pre-treated with a silane coupling agent in order to enhance the bond between the filler and the resin.

The filler(s) contained in the Base Part are typically present in the following amount(s):

Lower limit: at least 10 or at least 15 or at least 20 wt. %;
Upper limit: utmost 85 or utmost 80 or utmost 75 wt. %;
Range: 10 to 85 or 15 to 80 or 20 to 75 wt. %;
wt. % with respect to the amount of the Base Part.

The Base Part further comprises transition metal component(s).

The nature and structure of the transition metal component(s) is not particularly limited, unless the desired result cannot be achieved.

Suitable transition metal component(s) include organic and/or inorganic salt(s) of vanadium, chromium, manganese, iron, cobalt, nickel, and/or copper, with copper, iron and vanadium being sometimes preferred.

According to one embodiment, the transition metal component is a copper containing component.

The oxidation stage of copper in the copper containing component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper procetonate), copper ethylhexanoate, copper salicylate complexes of copper with thiourea, ethylenediaminetetraacetic acid and/or mixtures thereof. The copper compounds can be used in hydrated form or free of water.

Especially preferred are sometimes copper(II) acetate, copper bis(1-phenylpentan-1,3-dione) complex (copper procetonate), and copper ethylhexanoate.

According to one embodiment, the transition metal component is an iron containing component.

The oxidation stage of iron in the iron containing component(s) is preferably +2 or +3.

Typical examples of iron containing component(s) which can be used include salts and complexes of iron including Fe(III) sulfate, Fe(III) chloride, iron carboxylates, iron naphthenate, Fe(III) acetylacetonate including the hydrates of these salts.

According to one embodiment, the transition metal component is a vanadium containing component.

The oxidation stage of vanadium in the vanadium containing component(s) is preferably +4 or +5.

Typical examples of vanadium component(s) which can be used include salts and complexes of vanadium including vanadium acetylacetonate, vanadyl acetylacetonate, vanadyl stearate, vanadium naphthenate, vanadium benzoyl acetonate, vanadyl oxalate, bis(maltolato)oxovanadium (IV), oxobis(1-phenyl-1,3-butanedionate)vanadium (IV), vanadium (V) oxytriisopropoxide, ammon metavanadate (V), sodium metavanadate (V), vanadium pentoxide (V), divanadium tetraoxide (IV), and vanadyl sulfate (IV) and mixtures thereof, with vanadium acetylacetonate, vanadyl acetylacetonate, and bis(maltolato)oxovanadium (IV) being sometimes preferred.

The transition metal component(s) contained in the Base Part is typically present in the following amount, wherein the amount is calculated with respect to the weight of the transition metal compound:

Lower limit: at least 0.001 or at least 0.002 or at least 0.005 wt. %;

Upper limit: utmost 0.1 or utmost 0.08 or utmost 0.05 wt. %;

Range: 0.001 to 0.1 or 0.002 to 0.08 or 0.005 to 0.05 wt. %;

wt. % with respect to the amount of the Base Part.

The Base Part further comprises peroxide component(s), in particular organic peroxide(s).

Generally, all organic peroxide(s) can be used, if suitable to achieve the desired result.

In contrast to inorganic peroxides, organic peroxide(s) do not comprise metals or metal ions. Thus, organic peroxides typically only comprise C, O, H and optionally halogens (e.g. F, Cl, Br). Organic peroxides which can be used include di-peroxide(s) and hydroperoxide(s).

According to one embodiment, the organic peroxide is used in excess with respect to the weight of the component comprising the ascorbic acid moiety.

According to one embodiment, the organic peroxide is a di-peroxide, preferably a di-peroxide comprising the moiety $R_1$—O—O—$R_2$—O—O—$R_3$, with $R_1$ and $R_3$ being independently selected from H, alkyl (e.g. $C_1$ to $C_6$), branched alkyl (e.g. $C_1$ to $C_6$), cycloalkyl (e.g. $C_5$ to $C_{10}$), alkylaryl (e.g. $C_7$ to Cu) or aryl (e.g. $C_6$ to $C_{10}$) and $R_2$ being selected from alkyl (e.g. ($C_1$ to $C_6$) or branched alkyl (e.g. $C_1$ to $C_6$).

Examples of suitable organic di-peroxides include 2,2-Di-(tert.-butylperoxy)-butane and 2,5-Dimethyl-2,5-di-(tert-butylperoxy)-hexane and mixtures thereof.

According to another embodiment, the organic peroxide is a hydroperoxide, in particular a hydroperoxide comprising the structural moiety

R—O—O—H with R being (e.g. $C_1$ to $C_{20}$) alkyl, (e.g. $C_3$ to $C_{20}$) branched alkyl, (e.g. $C_6$ to $C_{12}$) cycloalkyl, (e.g. $C_7$ to $C_{20}$), alkylaryl (e.g. $C_6$ to $C_{12}$) or aryl (e.g. $C_6$ to $C_{12}$).

Examples of suitable organic hydroperoxides include t-butyl hydroperoxide, t-amyl hydroperoxide, p-diisopropylbenzene hydroperoxide, cumene hydroperoxide, pinane hydroperoxide, p-methane hydroperoxide and 1,1,3,3-tetramethylbutyl hydroperoxide and mixtures thereof.

Using hydroperoxides is sometimes preferred, in particular for formulating self-adhesive compositions.

Other peroxides which can be used are ketone peroxide(s), diacyl peroxide(s), dialkyl peroxide(s), peroxyketal(s), peroxyester(s) and peroxydicarbonate(s).

Examples of ketone peroxides include methyl ethyl ketone peroxide, methyl isobutyl ketone peroxide, methyl cyclohexanone peroxide, and cyclohexanone peroxide.

Examples of peroxyesters include alpha-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate (TBPIN), t-butylperoxy acetate, t-butylperoxy benzoate and t-butylperoxymaleic acid.

Examples of peroxidicarbonates include di-3-methoxy peroxidicarbonate, di-2-ethylhexyl peroxydicarbonate, bis (4-t-butylcyclohexyl)peroxidicarbonate, diisopropyl-1-peroxydicarbonate, di-n-propyl peroxidicarbonate, di-2-ethoxyethyl-peroxidicarbonate, and diallyl peroxidicarbonate.

Examples of diacyl peroxides include acetyl peroxide, benzoyl peroxide, decanoyl peroxide, 3,3,5-trimethylhexanoyl peroxide, 2,4-dichlorobenzoyl peroxide and lauroylperoxide.

Examples of dialkyl peroxiodes include di-t-butyl peroxide, dicumylperoxide, t-butylcumyl peroxide, 2,5-dimethyl-2,5-di(t-butylperpoxy)hexane, 1,3-bis(t-butylperoxyisopropyl)benzene and 2,5-dimethyl-2,5-di(t-butylperoxy)-3-hexane.

Examples of peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butylester.

The organic peroxide(s) contained in the Base Part is typically present in the following amounts:

Lower limit: at least 0.1 or at least 0.2 or at least 0.5 wt. %;

Upper limit: utmost 5 or utmost 4 or utmost 3 wt. %;

Range: 0.1 to 5 wt. % or 0.2 to 4 wt. % or 0.5 to 3 wt. %;

wt. % with respect to the amount of the Base Part.

If the amount of the organic peroxide(s) is too high, the setting time of the composition may be too fast.

If the amount of the organic peroxide(s) is too low, the setting time of the composition may be too slow.

The Base Part further comprises stabilizer component(s) comprising a free-radical moiety.

Adding a stabilizer may help to improve the storage stability of the dental composition, in particular, the storage stability of a dental composition comprising transition metal ion component(s) and also dental compositions comprising transition metal ion component(s) in combination with a peroxide.

Stabilizers which were found to be useful include those which comprise a free radical moiety or being selected from anaerobic stabilizers.

Free radical moieties include the moieties of 2,2-diphenyl-1-picrylhydrazyl (DPPH), 4-hydroxy-2,2,6,6-tetramethyl-piperidine 1-oxyl (TEMPOL), 2,2,6,6 Tetramethyl-piperidinyloxyl (TEMPO)

2,6-di-tert-butyl-α-(3,5-di-tert-butyl-4-oxo-2,5-cyclohexadien-1-ylidene)-p-tolyloxyl (Galvinoxyl), triphenylmethyl radical.

Stabilizers comprising as free radical moiety the structural moiety of TEMPOL or TEMPO are sometimes preferred. If desired, these stabilizers can be characterized by either of the following formulas:

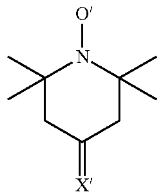

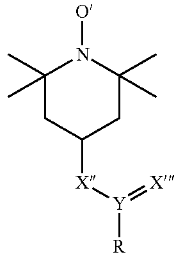

wherein X', X'', X''', Y and R independently of each other have the following meanings:

X'=O, S

X'', X'''=O, S or not present

Y=C, H or not present

R=H, alkyl, alkenyl, aryl, alkylaryl or arylalkyl having 1 to 12 C atoms each or not present.

In particular, the following stabilizers were found to be useful: 4-hydroxy-2,2,6,6-tetramethylpiperidine 1-oxyl (Prostab™ 5198), bis(2,2,6,6-tetramethylpiperidin-1-oxyl-4-yl) decanedioate (Prostab™ 5415), 4-methacryloyloxy-2,2,6,6-tetramethylpiperidine-1-oxyl, 4-amino-2,2,6,6-tetramethylpiperidine-1-oxyl, 4-acetamido-2,2,6,6-tetramethylpiperidine-1-oxyl, 4-oxo-2,2,6,6-tetramethylpiperidine-1-oxyl, 2,2-diphenyl-1-picrylhydrazyl (DPPH), 2,2-Di(4-tert-octylphenyl)-1-picrylhydrazyl and mixtures thereof.

On the other hand, the following stabilizers were found to be less useful for stabilizing a curable composition containing an initiator system comprising peroxide component(s) in combination with transition metal ion component(s):

Butylated hydroxy toluene (BHT), hydroquinone, hydroquinone monomethyl ether (MEHQ), tris(2,4-ditert-butylphenyl)phosphite (Irgafos™ 168), 4,6-bis(dodecylthiomethyl)-o-cresol (Irganox™ 1726), 4,6-bis(octylthiomethyl)-o-cresol (Irganox™ 1520 L), octadecyl-3-(3,5-di-tert.butyl-4-hydroxyphenyl)-propionate (Irganox™ 1076), thiodiethylene bis[3-(3,5-di-tert-butyl-4-hydroxyphenyl)propionate] (Irganox™ 1035), didodecyl 3,3'-thiodipropionate (Irganox™ PS 800 FL), 2',3-bis[[3-[3,5-di-tert-butyl-4-hydroxyphenyl]propionyl]]propionohydrazide (Irganox™ MD 1024), NOR-HALS like Flamestab™ NOR 116 FF), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, and 2-(2'-hydroxy-5'-methacryloxyethylphenyl)-2H-benzotriazole.

Using a too high amount of these stabilizers might cause undesired discoloration during storage. However, these stabilizers can nevertheless be used in addition, if desired.

Stabilizer(s) comprising a free-radical moiety contained in the Base Part are typically present in the following amount(s):

Lower limit: at least 0.005 or at least 0.01 or at least 0.02 wt. %;

Upper limit: utmost 0.3 or utmost 0.2 or utmost 0.1 wt. %;

Range: 0.005 to 0.3 or 0.01 to 0.2 or 0.02 to 0.1 wt. %;

wt. % with respect to the amount of the Base Part.

The composition contained in the Catalyst Part typically has a viscosity in the range of 5 to 60 Pa*s at 23° C.

A Catalyst Part having a viscosity in such a range can easily be mixed by using a static mixing cannula.

The composition contained in the Catalyst Part typically has a pH-value in a range of 5 to 7, if brought in contact with water (e.g. a wet pH-sensitive paper).

The Catalyst Part is typically provided as a paste.

The Catalyst Part comprises polymerizable component(s) without an acidic moiety.

The polymerizable component(s) without an acidic moiety contained in the Catalyst Part can be characterized by the same general formula used for describing the polymerizable component(s) without acidic moiety contained in the Base Part.

The polymerizable component(s) without an acidic moiety contained in the Catalyst Part can also be selected from those examples described for the Base Part.

The polymerizable component without an acidic moiety contained in the Catalyst Part is typically present in the following amount(s):

Lower limit: at least 5 or at least 10 or at least 20 wt. %;

Upper limit: utmost 70 or utmost 60 or utmost 50 wt. %;

Range: 5 to 70 or 10 to 60 or 20 to 50 wt. %;

wt. % with respect to the amount of the Catalyst Part.

The filler(s) contained in the Catalyst Part can be same or different to those which are contained in the Base Part.

The filler(s) contained in the Catalyst Part are typically present in the following amount(s):

Lower limit: at least 10 or at least 15 or at least 20 wt. %;

Upper limit: utmost 85 or utmost 80 or utmost 75 wt. %;

Range: 10 to 85 or 15 to 80 or 20 to 75 wt. %;

wt. % with respect to the amount of the Catalyst Part.

The Catalyst Part comprises an ascorbic acid component.

The component(s) comprising an ascorbic acid moiety include salts and esters of ascorbic acid, ethers, ketals, or acetals.

Suitable salts include the alkali metal and earth alkali metal salts like Na, K, Ca and mixtures thereof.

Esters of ascorbic acid include those which are formed by reacting one or more of the hydroxyl functions of ascorbic acid with a carboxylic acid, in particular the $C_2$ to $C_{30}$ carboxylic acid.

Suitable examples of $C_2$ to $C_{30}$ carboxylic acids include the fatty acids, like caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

In particular preferred are those ascorbic acid components, which can be easily dissolved in or mixed with the remaining resin matrix comprising polymerizable components without acidic moieties.

That is, using an ascorbic acid component having in addition a hydrophobic moiety can be preferred. Suitable hydrophobic moieties include saturated and unsaturated aliphatic residues (e.g. $C_2$ to $C_{30}$ or $C_{12}$ to $C_{30}$). Those ascorbic acid derivatives may also function as surface-active substances (substances having a so-called "head/tail structure").

Particularly preferred are ascorbyl palmitate, ascorbyl stearate, mixtures and salts thereof, in particular the alkaline and alkaline earth salts thereof.

The ascorbic acid component comprising an ascorbic acid moiety contained in the Catalyst Part is typically present in the following amounts:

Lower limit: at least 0.05 or at least 0.1 or at least 0.2 wt. %;

Upper limit: utmost 5 or utmost 3 or utmost 2 wt. %;

Range: 0.05 to 5 wt. % or 0.1 to 3 wt. % or 0.2 to 2 wt. %.

wt. % with respect to the amount of the Catalyst Part.

If the amount of the ascorbic acid component is too high, the setting time of the composition may be too fast.

If the amount of the ascorbic acid component is too low, the setting time of the composition may be too slow.

The Catalyst Part comprises a photo-initiator system.

The nature and structure of the photo-initiator system is not particularly limited unless the intended purpose is not negatively affected.

By incorporating a photo-initiator system, a composition is obtained which can be characterized as "dual curing", that is, it contains a redox-initiator system which is suitable to harden the composition without radiation ("dark-curing or self-curing") and a photo-initiator system which is suitable to harden the composition upon the application of radiation ("light-curing").

Suitable photo-initiator systems for free radical polymerization are generally known to the person skilled in the art dealing with dental materials.

Suitable photo-initiator systems often contain a sensitizer comprising alpha-alpha di-keto moiety, an anthraquinone moiety, a thioxanthone moiety or benzoin moiety. Sensitizers containing an alpha-alpha di-keto moiety are often preferred.

Typical photo-initiator systems comprise a combination of a sensitizer and a reducing agent or donor component, which is often referred to as photo-initiator system.

As sensitizer, those which can polymerize the polymerizable monomer(s) by the action of a visible light having a wavelength of from 390 nm to 830 nm are preferred.

Examples of sensitizers which can be used include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthra-quinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylamino-benzophenone.

As the reducing agent or donor component, tertiary amines and the like are generally used. Suitable examples of the tertiary amines include N,N-dimethyl-p-toluidine, N,N-dimethylaminoethyl methacrylate, triethanolamine, methyl 4-dimethylaminobenzoate, ethyl 4-dimethylaminobenzoate, methyldiphenylamine and isoamyl 4-dimethylaminobenzoate.

Moreover, ternary photopolymerization initiating systems consisting of a sensitizer, an electron donor and an onium salt as described in U.S. Pat. Nos. 6,187,833, 6,025,406, 6,043,295, 5,998,495, 6,084,004, 5,545,676 and WO 2009/151957 and U.S. Pat. No. 6,765,036 can be used. These references are included herein by reference.

In the ternary photo-initiator system, the first component is an iodonium salt, i.e., a diaryliodonium salt.

The iodonium salt is preferably soluble in the monomer and storage stable (i. e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as $Cl^-$, $Br^-$, r or $C_4H_5$ $SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photo-initiator system is a sensitizer.

The sensitizer desirably is soluble in the monomer and is capable of light absorption within the range of wavelengths of greater than 400 to 1200 nm, more preferably greater than 400 to 700 nm and most preferably greater than 400 to 600 nm.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers.

For example, a preferred class of ketone sensitizers has the formula: $ACO(X)_bB$, where X is CO or $CR^5$ $R^6$, where $R^5$ and $R^6$ can be the same or different, and can be hydrogen, alkyl, alkaryl or aralkyl, b is zero or one, and A and B different and can be substituted (having one or more non-interfering substituents) can be the same or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone and the like.

The third component of a ternary initiator system is a donor.

Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676. This reference is incorporated herein by reference.

Alternatively, free-radical initiators useful in the invention include the class of acylphosphine oxides and bisacylphosphine oxides.

Suitable acylphosphine oxides can be described by the general formula $$(R^9)2\text{-}P(=O)—C(=O)—R^{10}$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{19}$ is a hydrocarbyl group, an S-, O-, or N-containing five- or six-membered heterocyclic group, or a Z—C(=O)—P(=O)—$(R^9)_2$ group, wherein Z represents a divalent hydrocarbyl group such as alkylene or phenylene having from 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Examples can also be found e.g. in U.S. Pat. No. 4,737,593.

Suitable bisacylphosphine oxides can be described by the general formula

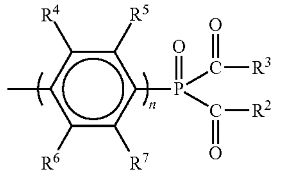

wherein n is 1 or 2, and $R^4$, $R^5$, $R^6$ and $R^7$ are H, C1-4 alkyl, C1-4 alkoxyl, F, Cl or Br; $R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or $R^2$ and $R^3$ are joined to form a ring containing from 4 to 10 carbon atoms and being optionally substituted by 1 to 6 C1-4 alkyl radicals.

Further examples include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bi s-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (formerly known as Irgacure™ 819, Ciba) is sometimes preferred.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate.

Commercially-available phosphine oxide photo-initiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (formerly known as Irgacure™ 1700, Ciba), 2-benzyl-2-(N,N-dimethylamino)-1-(4-morpholinophenyl)-1-butanone (formerly known as Irgacure™ 369, Ciba), bis(η5-2,4-cyclopentadien-1-yl)-bis(2,6-difluoro-3-(1H-pyrrol-1-yl)phenyl) titanium (formerly known as Irgacure™ 784 DC, Ciba), a 1:1 mixture, by weight, of bis(2,4,6-trimethylbenzoyl)phenyl phosphine oxide and 2-hydroxy-2-methyl-1-phenylpropane-1-one (formerly known as Darocur™ 4265, Ciba), ethyl-2,4,6-trimethylbenzylphenyl phosphine oxide (formerly known as Lucirin™ LR8893X, BASF), and Bis(2,4,6-trimethylbenzoyl)-phenylphosphine oxide (formerly known as Irgacure™ 819, BASF).

The sensitizing agent and reducing agent are typically present together in one part of the kit of parts described in the present text. Alternatively, the components of a photo-initiator system can be spread between The Base Part and the Catalyst Part.

For stability reasons, it can be preferred, if the photo-initiator system is contained in the Catalyst Part, i.e. the part containing the ascorbic acid component(s) thereof.

The Catalyst Part comprises stabilizer component(s) comprising a phosphite or sulfite moiety.

Preferred are sometimes organic stabilizer(s), that is, stabilizer(s) which are not salts.

Without wishing to be bound to a particular theory, it is believed that the solubility of the stabilizer in the composition and/or the pKs value of the stabilizer needs to be considered.

Using a stabilizer having a high solubility is sometimes preferred. Using less acidic stabilizers is sometimes preferred, as well.

It was found that the stabilizing effect of organic sulfite or organic phosphite stabilizers is sometimes better than those of inorganic sulfite or inorganic phosphite stabilizers.

According to one embodiment, the stabilizer(s) have a molecular weight of 80 to 800 or 120 to 700 g/mol.

The stabilizer(s) comprising a phosphite or sulfite moiety contained in the Catalyst Part is typically present in the following amount:

Lower amount: at least 0.01 or at least 0.05 or at least 0.1 wt. %;

Upper amount: up to 5 or up to 3 or up to 1 wt. %;

Range: from 0.01 to 5 wt. % or from 0.05 to 3 wt. % or from 0.1 to 1 wt. %;

wt. % with respect to the weight of the Catalyst Part.

Examples of inorganic phosphite(s) include calcium hypophosphite, sodium phosphite and mixtures thereof.

Examples of organic phosphite(s) include alkyl or aryl or alkyl-aryl (e.g. $C_1$ to $C_{40}$) phosphites, (e.g. di-ethylphosphite, di-butylphosphite, di-iso-propylphosphite, di-n-propylphosphite, tri-phenylphosphite, tri-allylphosphite, tris(2,4-di-tert.-butylphenyl)phosphite) (commercially available as Irgafos™ 168), bis(2,4-dicumylphenyl)pentaerythritol diphosphate (commercially available as Doverphos™ S-9228), bis-(2,4-di-t-butylphenol) pentaerythritol diphosphite (commercially available as Irgafos™126), phosphorous trichloride, reaction products with 1,1'-biphenyl and 2,4-bis(1,1-dimethylethyl)phenol (commercially available as Hostanox™ P-EPQ), and mixtures thereof.

Mixtures of organic and inorganic phosphites can also be used, if desired.

Examples of inorganic sulfite(s) include lithium sulfite, sodium sulfite, potassium sulfite, calcium sulfite, sodium bisulfite and mixtures thereof.

Examples of organic sulfite(s) include di-alkyl or aryl (e.g. $C_1$ to $C_{12}$) sulfites (e.g. diethyl sulfite, di-n-propyl sulfite, di-isoproply sulfite, glycol sulfite, 1,3-propylen sulfite), diallylsulfite and mixtures thereof.

Mixtures of organic and inorganic sulfites can also be used, if desired.

Mixtures of organic and inorganic phosphites and sulfites can also be used as well, if desired.

According to one embodiment, using stabilizers selected from organic sulfites, organic phosphites and mixtures thereof is preferred.

The ratio of the stabilizer component(s) comprising a free-radical moiety to the peroxide component(s) is typically in a range of 1:100 to 1:5 or 1:50 to 1:10 with respect to molar amounts.

Such a ratio can be beneficial for improving the reactivity of the dental composition.

The ratio of the stabilizer component(s) comprising a free-radical moiety to the transition metal component(s) calculated with respect to the weight of the transition metal ion is typically in a range of 100:1 to 5:1 or 75:1 to 10:1 with respect to weight.

Such a ratio can be beneficial for improving the colour stability of the dental composition.

The combination of the following ratios was found to be particularly beneficial for obtaining a storage stable dental composition:

ratio of the stabilizer component(s) comprising a free-radical moiety to the peroxide component(s) being in a range of 1:100 to 1:5 with respect to molar amounts, ratio of the stabilizer component(s) comprising a free-radical moiety to the transition metal component(s) calculated with respect to the weight of the transition metal ion being in a range of 100:1 to 5:1.

According to one embodiment, upon mixing the Base Part and the Catalyst Part the dental composition comprises or consists essentially of the respective components in the following amounts:

polymerizable component(s) with an acidic moiety: 0 to 20 wt. %, polymerizable component(s) without an acidic moiety: 5 to 50 wt. %, filler(s): 5 to 80 wt. %, transition metal component(s): 0.0005 to 0.05 wt. %, peroxide component(s): 0.05 to 2.5 wt. %, stabilizer component(s) comprising a free-radical moiety: 0.0025 to 0.15 wt. %, ascorbic acid component: 0.025 to 2.5 wt. %, photo-initiator system: 0.05 to 2.5 wt. %, stabilizer component(s) comprising a phosphite or sulfite moiety: 0.005 to 2.5 wt. %, wt. % with respect to the weight of the whole composition.

According to another embodiment, upon mixing the Base Part and the Catalyst Part the dental composition comprises or consists essentially of the respective components in the following amounts:

polymerizable component(s) with an acidic moiety: 1 to 20 wt. %, polymerizable component(s) without an acidic moiety: 5 to 50 wt. %, filler(s): 20 to 80 wt. %, transition metal component(s) calculated with respect to the weight of the transition metal compound: 0.0005 to 0.05 wt. %, peroxide component(s): 0.05 to 2.5 wt. %, stabilizer component(s) comprising a free-radical moiety: 0.025 to 0.15 wt. %, ascorbic acid component: 0.025 to 2.5 wt. %, photo-initiator system: 0.05 to 2.5 wt. %, stabilizer component(s) comprising a phosphite or sulfite moiety: 0.05 to 2.5 wt. %, wt. % with respect to the weight of the whole composition.

The dental composition described in the present text may also comprise solvent(s).

Adding solvent(s) or co-solvent(s) may help to adjust the viscosity and consistency of the composition.

Examples of solvents include, but are not limited to linear, branched or cyclic, saturated or unsaturated alcohols, ketones, esters, ethers or mixtures of two or more of said type of solvents with 2 to 10 C atoms. Preferred alcoholic solvents include methanol, ethanol, iso-propanol and n-propanol.

Other suitable organic solvents are THF, acetone, methyl ethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

If present, the solvent(s) can be present in the Base Part or the Catalyst Part or in both parts.

If present, the solvent(s) is typically present in the following amount(s):

Lower limit: at least 1 or at least 2 or at least 5 wt. %;

Upper limit: utmost 20 or utmost 15 or utmost 10 wt. %;

Range: 1 to 20 or 2 to 15 or 5 to 10 wt. %;

wt. % with respect to the amount of the dental composition.

The dental composition described in the present text may comprise in addition the following additive(s) alone or in combination.

Additives of adjuvants which can be used include fluoride release agents, photo-bleachable colorants, dyes, and other ingredients well known to those skilled in the art.

Examples of photo-bleachable colorants include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photo-bleachable colorants can be found in U.S. Pat. No. 6,444,725 (Tom et al.).

Examples of fluoride release agents are naturally occurring or synthetic fluoride minerals such as sodium fluoride, simple and complex inorganic fluoride salts such as potassium zinc fluoride and potassium hexa fluorotitanate, simple and complex organic fluoride salts such as tetraethylammonium tetrafluoroborate or combinations thereof. These fluoride sources can optionally be treated with surface treatment agents.

If present, the additive(s) can be present in the Base Part or the Catalyst Part or in both parts.

If present, additive(s) are present in the following amount(s):

Lower limit: at least 0.01 or at least 0.1 or at least 0.2 wt. %;

Upper limit: utmost 5 or utmost 3 or utmost 2 wt. %;

Range: 0.01 to 5 or 0.1 to 3 or 0.2 to 2 wt. %;

wt. % with respect to the amount of the dental composition.

The dental composition described in the present text can also be characterized by the following features alone or in combination after mixing and hardening the Base Part and the Catalyst Part: Flexural strength according to ISO 4049: 2010: 80 to 200 MPa and/or E-modulus according to ISO 4049:2010: 3,000 to 7,000 MPa.

Further embodiments of the invention are described below:

Embodiment 1 is directed to a dental composition comprising a Base Part and a Catalyst Part to be mixed before use, the Base Part comprising or consisting essentially of polymerizable component(s) with an acidic moiety in an amount of 0 to 20 wt. %, polymerizable component(s) without an acidic moiety in an amount of 5 to 70 wt. %, filler(s) in an amount of 10 to 85 wt. %, transition metal component(s) selected from organic salts of copper, vanadium and iron and mixtures thereof, peroxide component(s) selected from di-peroxide(s), hydroperoxide(s), ketone peroxide(s), peroxyester(s), peroxydicarbonate(s), diacyl peroxide(s), dialkyl peroxide(s), peroxyketal(s), and mixtures thereof, stabilizer component(s) comprising a free-radical moiety selected from 2,2-diphenyl-1-picrylhydrazyl (DPPH), 4-hydroxy-2,2,6,6-tetramethyl-piperidine 1-oxyl (TEMPOL), 2,2,6,6 Tetramethyl-piperidinyloxyl (TEMPO) 2,6-di-tert-butyl-α-(3,5-di-tert-butyl-4-oxo-2,5-cyclohexa-dien-1-ylidene)-p-tolyloxyl (Galvinoxyl), triphenylmethyl radical, and optionally additive(s), the Catalyst Part comprising or consisting essentially of polymerizable component(s) without an acidic moiety in an amount of 5 to 70 wt. %, filler(s) in an amount of 10 to 85 wt. %, ascorbic acid component selected from $C_2$ to $C_{30}$ carboxylic acid esters of ascorbic acid, alkali and earth alkali salts of ascorbic acid and mixtures thereof, photo-initiator system comprising a sensitizer and a reducing agent or donor component, stabilizer component(s) comprising a phosphite or sulfite moiety selected from organic phosphites, organic sulfites and mixtures thereof, and optionally additive(s), wt. % with respect to the weight of the whole composition.

Embodiment 2 is directed to a dental composition comprising a Base Part and a Catalyst Part to be mixed before use, the Base Part comprising or consisting essentially of polymerizable component(s) with an acidic moiety in an amount of 0.5 to 20 wt. %, polymerizable component(s) without an acidic moiety in an amount of 5 to 70 wt. %, filler(s) in an amount of 10 to 85 wt. %, transition metal component(s) selected from organic salts of copper, and mixtures thereof, peroxide component(s) selected from di-peroxide(s), hydroperoxide(s), and mixtures thereof, stabilizer component(s) comprising a free-radical moiety selected from 2,2-diphenyl-1-picrylhydrazyl (DPPH), 4-hydroxy-2,2,6,6-tetramethyl-piperidine 1-oxyl (TEMPOL), 2,2,6,6 Tetramethyl-piperidinyloxyl (TEMPO) 2,6-di-tert-butyl-α-(3,5-di-tert-butyl-4-oxo-2,5-cyclohexa-dien-1-ylidene)-p-tolyloxyl (Galvinoxyl), triphenylmethyl radical, and optionally additive(s), the Catalyst Part comprising or consisting essentially of polymerizable component(s) without an acidic moiety in an amount of 5 to 70 wt. %, filler(s) in an amount of 10 to 85 wt. %, ascorbic acid component selected from $C_2$ to $C_{30}$ carboxylic acid esters of ascorbic acid, alkali and earth alkali salts of ascorbic acid and mixtures thereof, photo-initiator system comprising a sensitizer and a reducing agent or donor component, stabilizer component(s) comprising a phosphite or sulfite moiety selected from organic phosphites, organic sulfites and mixtures thereof, and optionally additive(s), wt. % with respect to the weight of the whole composition.

Embodiment 3 is directed to a dental composition comprising a Base Part and a Catalyst Part to be mixed before use, the Base Part comprising or consisting essentially of polymerizable component(s) with an acidic moiety, polymerizable component(s) without an acidic moiety, filler(s), transition metal component(s) selected from organic salts of copper, and mixtures thereof, peroxide component(s) selected from di-peroxide(s), hydroperoxide(s), and mixtures thereof, stabilizer component(s) comprising a free-radical moiety selected from 2,2-diphenyl-1-picrylhydrazyl (DPPH), 4-hydroxy-2,2,6,6-tetramethyl-piperidine 1-oxyl (TEMPOL), 2,2,6,6 Tetramethyl-piperidinyloxyl (TEMPO) 2,6-di-tert-butyl-α-(3,5-di-tert-butyl-4-oxo-2,5-cyclohexa-dien-1-ylidene)-p-tolyloxyl (Galvinoxyl), triphenylmethyl radical, and optionally additive(s), the Catalyst Part comprising or consisting essentially of polymerizable component(s) without an acidic moiety, filler(s), ascorbic acid component selected from $C_2$ to $C_{30}$ carboxylic acid esters of ascorbic acid, and mixtures thereof, photo-initiator system comprising a sensitizer and a reducing agent or donor component, stabilizer component(s) comprising a phosphite moiety, and optionally additive(s).

The respective components are those described in the present text.

The dental composition described in the present text does typically not contain the following components alone or in combination:

water in an amount of more than 2 wt. % or more than 1 wt. %;

halogenated solvents in an amount of more than 2 wt. % or more than 1 wt. % or more than 0.5 wt. %;

thiourea components in an amount of more than 2 wt. % or more than 1 wt. % or more than 0.5 wt. %;

wt. % with respect to the whole composition.

These component(s) are typically not willfully added to the dental composition and thus not present.

However, the dental composition may comprise traces of these components, the presence of which is sometimes unavoidable as they may be contained in the raw materials used for preparing the dental composition described in the present text.

The invention is also related to a process for producing the dental composition described in the present text.

The composition described in the present text can be produced as follows:

providing the components of the composition, mixing the components.

The temperature at which the production process is conducted is not particularly limited.

The temperature used should be below the boiling point of the composition at normal pressure (1,013 mbar). Usually the process can be conducted at a temperature in the range of 5° C. to 100° C. or within a range of 10° C. to 80° C. Conducting the process under ambient temperature (e.g. about 23° C.) is possible as well.

The atmosphere under which the production process is conducted is not particularly limited, either.

Usually, the production process is conducted under ambient conditions. Depending on the components used, conducting the production process under inert conditions can be recommended. In this respect, a nitrogen or argon atmosphere could be useful.

The pressure under which the production process of the invention can be conducted is not particularly limited, either. However, the process is typically conducted under ambient pressure (about 1013 mbar).

The manner and sequence how the components are added is not particularly limited. However, typically the production process starts with providing the liquid components (such as polymerizable components without an acidic moiety and polymerizable components with an acidic moiety), adding the stabilizer components and initiator components followed by the addition of the filler(s).

Mixing or dispersing of components can be accomplished using a device such as magnetic stirrers, mechanical stirrers, dissolvers, ball mills, attritor mills or high shear equipment.

The Catalyst Part and the Base Part of dental composition are typically stored in a packaging device during storage.

The Catalyst Part and the Base Part described in the present text may be contained in separate sealable vessels (e.g. made out of plastic or glass).

For use, the practitioner may take adequate portions of the compositions contained from the vessels and mix the portions by hand on a mixing plate.

According to a preferred embodiment, the Catalyst Part and the Base Part are contained in separate compartments of a storage device.

The storage device typically comprises two compartments for storing the respective parts, each compartment being equipped with a nozzle for delivering the respective part and a piston movable in the compartment. Once delivered in adequate portions, the parts can then be mixed by hand on a mixing plate.

According to another preferred embodiment, the storage device has an interface for receiving a static mixing tip. The mixing tip is used for mixing the respective pastes. Static mixing tips are commercially available e.g. from Sulzer-Mixpac company.

Suitable storage devices include cartridges, syringes and tubes.

Cartridges which can be used are described e.g. in US 2007/0090079 A1 or U.S. Pat. No. 5,918,772, the disclosure of which is incorporated by reference. Some of the cartridges which can be used are commercially available e.g. from SulzerMixpac company (Switzerland). Static mixing tips which can be used are described e.g. in US 2006/0187752 A1 or in U.S. Pat. No. 5,944,419, the disclosure of which is incorporated by reference. Mixing tips which can be used are commercially available from SulzerMixpac company (Switzerland), as well.

Other suitable storing devices are described e.g. in WO 2010/123800 A1 (3M), WO 2005/016783 A1 (3M), WO 2007/104037 A1 (3M), WO 2009/061884 A1 (3M), in particular the device shown in FIG. 14 of WO 2009/061884 (3M) or WO 2015/073246 (3M), in particular the device shown in FIG. 1 of WO 2015/07346. Those storing devices have the shape of a syringe. The content of these references is herewith incorporated by reference, as well.

Alternatively, but less preferred, paste/paste compositions described in the present text can be provided in two individual syringes and the individual pastes can be mixed by hand prior to use.

Thus, the invention is also directed to a device for storing the kit of parts described in the present text, the device comprising two compartments, Compartment A and Compartment B, Compartment A containing the Catalyst Part and Compartment B containing the Base Part, the Catalyst Part and the Base Part being as described in the present text, Compartment A and Compartment B both comprising a nozzle or an interface for receiving an entrance orifice of a static mixing tip.

The mixing ratio of the Base Part and the Catalyst Part is typically from 5:1 to 1:1 with respect to volume, preferably from 2:1 to 1:2, more preferably 1:1.

The invention also relates to a process of curing the dental composition described in the present text.

Such a process typically comprises the following steps: The Catalyst Part and the Base Part are provided. The Catalyst Part and the Base Part are mixed. The obtained mixture is applied to a dental surface.

When brought in contact with each other, the redox-initiator components contained the respective parts initiate the curing of the curable components of the curable composition.

In addition, the curing of the curable composition can be further accelerated by applying radiation with a wave length being suitable for the photo-initiator system used.

Thus, the dental composition described in the present text is intended for use in a process of treating or restoring hard dental tissue of a living human being or animal, the process comprising the steps of

- mixing the Base Part and the Catalyst Part to obtain a Mixed Part,
- applying a portion of the Mixed Part to the surface of the hard dental tissue,
- optionally applying radiation to the portion of the Mixed Part.

Thus, the dental composition described in the present text is a so-called dual-curable composition, i.e. a composition which contains two curing systems, a redox-curing system and a photo-initiator system The dental composition described in the present text is in particular useful as bulk fill dental composite, dental resin cement, core build-up dental material or self- and dual cure dental adhesive. Thus, the dental composition can be used in a process of treating or restoring hard dental tissue of a human being or animal by providing the dental composition in the form of a bulk fill dental composite, dental resin cement, core build-up dental material or self- and dual cure dental adhesive.

The invention is also directed to a kit of parts comprising or consisting essentially of or consisting of the dental composition described in the present text and the following items alone or in combination: dental filling composite; dental sealant; dental cement; dental mill blank; dental etchant; dental try-in paste; dental fibre post; dental adhesive and/or instruction for use. The combination of the dental composition described in the present text with a dental filling composite or a dental cement is sometimes preferred.

A further aspect of the invention is directed to the use of a stabilizer comprising a free-radical moiety for stabilizing an initiator system comprising or consisting essentially of or consisting of peroxide component(s) in combination with transition metal ion component(s), optionally in combination with a photo-initiator system as described in the present text.

A further embodiment of the invention relates to an initiator system which is described in the present text and which can be used for curing a composition comprising polymerizable component(s) with an acidic moiety.

Such an initiator system comprises transition metal component(s), peroxide component(s), stabilizer component(s) comprising a free-radical moiety, ascorbic acid component(s), a photo-initiator system, and stabilizer component(s) comprising a phosphite or sulfite moiety wherein the components are as described in the present text.

A preferred embodiment of such an initiator system comprises or consists essentially of or consists of

- transition metal component(s) selected from organic salts of copper, vanadium and iron and mixtures thereof, preferably organic salts of copper,
- peroxide component(s) selected from di-peroxide(s), hydroperoxide(s), ketone peroxide(s), diacyl peroxide(s), dialkyl peroxide(s), peroxyketal(s), peroxyester(s) and peroxydicarbonate(s), preferably di-peroxide(s), hydroperoxide(s),
- stabilizer component(s) comprising a free-radical moiety selected from 2,2-diphenyl-1-picrylhydrazyl (DPPH), 4-hydroxy-2,2,6,6-tetramethyl-piperidine 1-oxyl (TEMPOL), 2,2,6,6 Tetramethyl-piperidinyloxyl (TEMPO) 2,6-di-tert-butyl-α-(3,5-di-tert-butyl-4-oxo-2,5-cyclohexadien-1-ylidene)-p-tolyloxyl (Galvinoxyl), triphenylmethyl radical, and mixtures thereof,
- ascorbic acid component(s), preferably esters of ascorbic acid,
- a photo-initiator system comprising a sensitizer and a donor component,
- and stabilizer component(s) comprising a phosphite or sulfite moiety, preferably a stabilizer component(s) comprising a phosphite moiety.

The complete disclosures of the patents, patent documents, and publications cited herein are incorporated by reference in their entirety as if each were individually incorporated. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

Examples

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Viscosity of Single Pastes

If desired, the viscosity can be measured using a Physica MCR 301 Rheometer (Anton Paar, Graz, Austria) with a cone/plate geometry PP15 under controlled shear rate at 23° C. The diameter is 15 mm. The shear rate is increased logarithmically from 0.001 $s^{-1}$ to 1,000 $s^{-1}$ with a total of 60 data points being collected. The viscosity determined at 100 $s^{-1}$ is used for characterization.

Viscosity of Mixed Pastes

If desired, the viscosity can be measured using a Physica MCR 301 Rheometer (Anton Paar, Graz, Austria) with a plate/plate geometry PP8 under controlled shear rate at 28° C. The diameter is 8 mm. The viscosity is measured with a constant shear rate of 10 $s^{-1}$ with a total of 17 data points being collected. The viscosity of data point 17 is used for characterization.

pH-Determination

If desired, the pH can be determined by using a wet pH sensitive paper.

Flexural Strength (FS) and E-Modulus (EM)

This measurement was conducted according to ISO 4049: 2010.

Color Value Measurement (CVM)

Delrin molds with 1.5 mm height and 15 mm in diameter were filled with approximately 0.6 g of base paste using two cover glasses. The L*, a*, b* and opacity values were measured with a Gretag McBeth Color i7 device using the following parameters: Ulbricht's Sphere; D65, 10° viewer; aperture: 10 mm, area view: 6 mm; remission; wavelength: 360-750 nm.

A b* value of the base paste in the range of 0 to 15 and a delta b* value during storage of the base paste in the range of 0 to 7 was found to meet the requirements of an aesthetic dental composition.

Stability Test for Auto-Polymerization (APT)

Base pastes were stored at 50° C. in PE-cartridges and visually inspected. When it was not possible to extrude the paste from the cartridge anymore, it was rated as polymerized.

Materials

Abbreviations

- GPDM: glycerol phosphate dimethacrylate
- Methacrylates: mixture of urethane dimethacrylate (Plex™ 6661) and triethylene glycol dimethacrylate
- UDMA: urethane dimethacrylate (Plex™ 6661)
- $YbF_3$: ytterbium trifluoride
- Sr glass: GM32087 from Schott, silane treated
- R805: silane treated fumed silica from Evonik AG
- Pigments: color pigments; fluorescent pigments
- Cu procetonate: copper bis(1-phenylpentane-1,3-dionate)
- Cu ethylhexanoate: copper bis(2-ethylhexanoate)
- TBPIN: tert.-butylperoxy-3,5,5-trimethylhexanoate
- CPQ: D,L-camphorquinone
- EDMAB: ethyl 4-dimethylaminobenzoate
- Accelerator: amine hydrochloride salt
- ASP: ascorbic acid palmitate
- TEMPOL: 4-Hydroxy-2,2,6,6-tetramethylpiperidine 1-oxyl
- BHT: 2,6-di-tert.-butyl-4-methylphenol (butylated hydroxytoluene)
- PMP-OH: pentamethyl-4-piperidinol
- Hostanox™: phosphorous trichloride, reaction products with 1,1-biphenyl and 2,4-bis(1,1-dimethylethyl)phenol,
- TPP: triphenylphosphite The following base pastes were prepared by mixing the respective components (the amounts are given in parts by weight):

TABLE 1

| Base Paste | I.E. 1 | C.E. 1 | C.E. 2 | C.E. 3 |
|---|---|---|---|---|
| Components | | | | |
| GPDM | 4 | 4 | 4 | — |
| Methacrylates | 28.29 | 28.29 | 28.29 | 32.29 |
| $YbF_3$ | 9 | 9 | 9 | — |
| Sr glass | 55 | 55 | 55 | 65 |
| Cu-procetonate | 0.01 | 0.01 | 0.01 | — |
| Cu-ethylhexanoate | — | — | — | 0.01 |
| R805 | 2 | 2 | 2 | 1 |
| TEMPOL | 0.2 | — | — | — |
| BHT | — | 0.2 | — | 0.2 |
| PMP-OH | — | — | 0.2 | — |
| TBPIN | 1.5 | 1.5 | 1.5 | 1.5 |

TABLE 1-continued

| Base Paste | I.E. 1 | C.E. 1 | C.E. 2 | C.E. 3 |
|---|---|---|---|---|
| CVM after 1 year storage @ RT | | | | |
| L* | 82.91 | 82.06 | 83.81 | 77.75 |
| a* | 0 | −8.25 | −0.67 | −2.8 |
| b* | 12.89 | 51.2 | 7.58 | 62.45 |
| Opacity | 88.82 | 85.67 | 88.65 | 88.72 |
| Delta b* | 1.77 | 37.58 | 6.21 | 50.00 |
| Stability @ 50° C. (APT) | >92 d | >92 d | 14 d | >92 d |

I.E = Inventive Example;
C.E. = Comparative Example

The following catalyst pastes were prepared by mixing the respective components (the amounts are given in parts by weight):

TABLE 2

| Catalyst Paste Components | I.E. 1 | C.E. 1 | C.E. 2 | C.E. 3 |
|---|---|---|---|---|
| pigments | 0.092 | 0.100 | 0.100 | — |
| CPQ | 0.1 | 0.1 | 0.1 | 0.05 |
| EDMAB | 0.399 | 0.399 | 0.399 | 0.2 |
| UV-stabilizer | 0.2 | 0.2 | 0.2 | 0 |
| BHT | 0.04 | 0.015 | 0.015 | 0.015 |
| Methacrylates | 34.004 | 33.526 | 33.526 | 33.435 |
| Hostanox ™ | 0.16 | 0.08 | 0.08 | 0.075 |
| TPP | — | 0.498 | 0.498 | 0.025 |
| ASP | 0.698 | 0.698 | 0.98 | 0.77 |
| Accelerator | 0.02 | 0.106 | 0.106 | 0 |
| $YbF_3$ | 8.972 | 8.97 | 8.97 | 9.00 |
| R805 | 0.535 | 0.538 | 0.538 | 1.5 |
| Sr glass | 54.78 | 54.77 | 54.77 | 55.00 |

To obtain a curable composition for determination of flexural strength and E-Modulus, equal portions by volume of the base paste were mixed with the catalyst paste.

TABLE 3

| Mixed paste | | | | |
|---|---|---|---|---|
| FS, light-cure [MPa] | 118 ± 10 | 129 ± 6 | 131 ± 11 | 118 ± 6 |
| EM, light-cure [MPa] | 6,346 ± 189 | 6,312 ± 314 | 6,320 ± 215 | 5,951 ± 273 |
| FS, self-cure [MPa] | 104 ± 11 | 110 ± 18 | 138 ± 7 | 109 ± 8 |
| EM, self-cure [MPa] | 4,608 ± 135 | 6,015 ± 141 | 6,220 ± 123 | 5,685 ± 152 |

As can be seen from Table 3, all compositions yielded flexural strength values in the range of 120 MPa (light cure mode), >100 MPa (self-cure mode) and E-Moduli in the range of 6,000 MPa (light cure mode), >4,600 MPa (self-cure mode).

A base paste using a sterically hindered amine as stabilizer (PMP-OH; Comp. Ex. 2; Table 1) did not show substantial discoloration upon storage (delta b* value of 6.21), but auto-polymerized after 14 days at 50° C.

Base pastes using a phenolic stabilizer (BHT) and different copper salts (Comp. Ex. 1 and 3; Table 1) did not auto-polymerize for more than 92 days at 50° C. but showed discoloration upon storage (b* values of 51.2 and 62.45, respectively).

A base paste using a stabilizer comprising a free radical (TEMPOL; Ex. 1; Table 1) did not show substantial discoloration upon storage (b* value of 12.89) and did not auto-polymerize for more than 92 days at 50° C.

The invention claimed is:

1. A dental composition comprising a Base Part and a Catalyst Part to be mixed before use, the Base Part comprising:

polymerizable component(s) without an acidic moiety, optionally polymerizable component(s) with an acidic moiety, filler(s), copper (II) salt transition metal component(s), peroxide component(s), stabilizer component(s) comprising a free-radical moiety represented by Formula I:

(I)

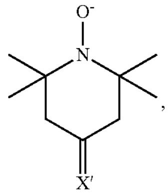

wherein:

X' is O or S; or stabilizer component(s) comprising a free-radical moiety represented by Formula II:

(II)

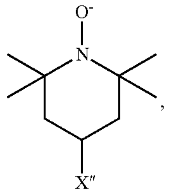

wherein:

X" is —H, —OH, —SH, —OR, or —SR, and

R is —H, $C_{1-12}$ alkyl, $C_{1-12}$ alkenyl, $C_{1-12}$ alkylaryl, or $C_{1-12}$ arylalkyl; or stabilizer component(s) comprising a free-radical moiety represented by Formula III:

(III)

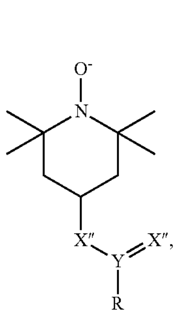

wherein:

X" is —O— or —S—,

Y is C and

R is —H, $C_{1-12}$ alkyl, $C_{1-12}$ alkenyl, $C_{1-12}$ alkylaryl, or $C_{1-12}$ arylalkyl; or stabilizer component(s) comprising a free-radical moiety selected from 4-amino-2,2,6,6-tetramethylpiperidine-1-oxyl and 4-acetamido-2,2,6,6-tetramethylpiperidine-1-oxyl, the Catalyst Part comprising:

polymerizable component(s) without an acidic moiety, filler(s), ascorbic acid component, photo-initiator system, stabilizer component(s) comprising a phosphite or sulfite moiety.

2. The dental composition according to claim 1, the ratio of the stabilizer component(s) comprising a free-radical moiety to the peroxide component(s) being in a range of 1:100 to 1:5 with respect to molar amounts.

3. The dental composition according to claim 1, the Base Part and the Catalyst Part being provided in a volume ratio of 10:1 to 1:1.

4. The dental composition according to claim 1, the stabilizer component(s) comprising a free-radical moiety containing a moiety selected from 4-hydroxy-2,2,6,6-tetramethyl-piperidine 1-oxyl, 2,2,6,6-Tetramethyl-piperidinyloxyl, and a combination thereof.

5. The dental composition according to claim 1, the stabilizer component(s) comprising a phosphite or sulfite moiety being selected from organic phosphite stabilizer(s), organic sulfite stabilizer(s) and mixtures thereof.

6. The dental composition according to claim 1, the peroxide component(s) being selected from di-peroxide(s), hydroperoxide(s), ketone peroxide(s), peroxyester(s), peroxydicarbonate(s), diacyl peroxide(s), dialkyl peroxide(s), peroxyketal(s), and mixtures thereof.

7. The dental composition according to claim 1, the copper salt transition metal ion component(s) being selected from copper bis (1-phenylpentane-1,3-dionate), copper bis (2-ethylhexanoate), and a combination thereof.

8. The dental composition according to claim 1 comprising the respective components in the following amounts:

polymerizable component(s) without an acidic moiety: 5 to 50 wt. %, polymerizable component(s) with an acidic moiety: 0 to 20 wt. %, filler(s): 5 to 80 wt. %, copper (II) salt transition metal component(s): 0.0005 to 0.05 wt. %, peroxide component(s): 0.05 to 2.5 wt. %, stabilizer component(s) comprising a free-radical moiety: 0.0025 to 0.15 wt. %, ascorbic acid component: 0.025 to 2.5 wt. %, photo-initiator system: 0.05 to 3 wt. %, stabilizer component(s) comprising a phosphite or sulfite moiety: 0.005 to 2.5 wt. %, wt. % with respect to the weight of the whole composition.

9. The dental composition according to claim 1, the Base Part comprising polymerizable component(s) with an acidic moiety in an amount of 0 to 20 wt. %, polymerizable component(s) without an acidic moiety in an amount of 5 to 70 wt. %, filler(s) in an amount of 10 to 85 wt. %, copper (II) salt transition metal component(s); selected from copper bis (1-phenylpentane- 1,3-dionate), copper bis (2-ethylhexanoate), and a combination thereof, peroxide component(s), selected from di-peroxide(s), hydroperoxide(s), ketone peroxide(s), peroxyester(s), peroxydicarbonate(s), diacyl peroxide(s), dialkyl peroxide(s), peroxyketal(s), and mixtures thereof, stabilizer component(s) comprising a free-radical moiety selected from 4-hydroxy-2,2,6,6-tetramethyl-piperidine 1-oxyl and 2,2,6,6 Tetramethyl-piperidinyloxyl, the Catalyst Part comprising polymerizable component(s) without an acidic moiety in an amount of 5 to 70 wt. %, filler(s) in an amount of 10 to 85 wt. %, ascorbic acid component selected from $C_2$ to $C_{30}$ carboxylic acid esters of ascorbic acid, alkali and earth alkali salts of ascorbic acid, alkaline and alkaline earth salts of ascorbic acid esters, and mixtures thereof, photo-initiator system comprising a sensitizer and a reducing agent or donor component, stabilizer component(s) comprising a phosphite or sulfite moiety, selected from organic phosphites, organic sulfites and mixtures thereof, wt. % with respect to the weight of the whole composition.

10. The dental composition according to claim 1 contained in a storage device, the storage device comprising two compartments for storing the respective parts, each compartment being equipped with a nozzle for delivering the respective part and a piston movable in the compartment.

11. The dental composition according to claim 1, for use in a process of treating or restoring hard dental tissue of a human being or animal, the process comprising the steps of mixing the Base Part and the Catalyst Part to obtain a Mixed Part, applying at least a portion of the Mixed Part to the surface of the hard dental tissue, optionally applying radiation to the portion of the Mixed Part.

12. The dental composition according to claim 1 for use in a process of treating or restoring hard dental tissue of a human being or animal, wherein the dental composition is used as bulk fill dental composite, dental resin cement, core build-up dental material or self-and dual cure dental adhesive.

13. A kit of parts comprising the dental composition as described in claim 1 and at least one of the following items: dental filling composite; dental sealant; dental cement; dental mill blank; dental etchant; dental adhesive; dental try-in paste; dental fibre post.

14. The dental composition of claim 1, the copper salt transition metal component(s) selected from organic salts.

15. The dental composition of claim 1, the copper (II) salt transition metal component(s) selected from copper bis (1-phenylpentane-1,3-dionate), copper bis (2-ethylhexanoate), and a combination thereof, and the stabilizer component(s) comprising a free-radical moiety selected from 4-hydroxy-2.2.6.6-tetramethyl-piperidine-1-oxyl, 2,2,2,6 tetramethyl-piperidinyloxyl, and a combination thereof.

16. The dental composition of claim 14, the stabilizer component(s) comprising a free-radical moiety selected from 4-hydroxy-2,2,6,6-tetramethyl-piperidine-1-oxyl, 2,2,6,6 tetramethyl-piperidinyloxyl, and a combination thereof.

17. The dental composition of claim 1, the stabilizer component(s) comprising a free-radical moiety selected from 4-hydroxy-2,2,6,6-tetramethyl-piperidine-1-oxyl, 2,2,6,6 tetramethyl-piperidinyloxyl, and a combination thereof, and the peroxide component(s) being a peroxyester.

18. The dental composition of claim 1, the peroxide component(s) being a peroxyester selected from alpha-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate, t-butylperoxymaleic acid, and a combination thereof.

19. The dental composition of claim 1, the ascorbic acid component being an ascorbic acid ester of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, or docosahexaenoic acid.

20. The dental composition of claim 1, the copper (II) salt transition metal component(s) selected from copper bis (1-phenylpentane-1,3-dionate), copper bis (2-ethylhexanoate), and a combination thereof, the stabilizer component(s) comprising a free-radical moiety selected from 4-hydroxy-2,2,6,6-tetramethyl-piperidine-1-oxyl, 2,2,6,6 tetramethyl-piperidinyloxyl, and a combination thereof, the peroxide component(s) being a peroxyester selected from alpha-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate, t-butylperoxymaleic acid, and a combination thereof, and the ascorbic acid component being an ascorbic acid ester of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, or docosahexaenoic acid.

* * * * *